(12) United States Patent
Chen et al.

(10) Patent No.: US 11,471,160 B2
(45) Date of Patent: Oct. 18, 2022

(54) HANDLE ASSEMBLY AND STAPLER INCLUDING THE SAME

(71) Applicant: TOUCHSTONE INTERNATIONAL MEDICAL SCIENCE CO., LTD., Jiangsu (CN)

(72) Inventors: Zhi Chen, Jiangsu (CN); Yi Guo, Jiangsu (CN); Jiang Lin, Jiangsu (CN); Xiaowei Xu, Jiangsu (CN)

(73) Assignee: TOUCHSTONE INTERNATIONAL MEDICAL SCIENCE CO., LTD.

( * ) Notice: Subject to any disclaimer, the term of this patent is extended or adjusted under 35 U.S.C. 154(b) by 189 days.

(21) Appl. No.: 16/957,553

(22) PCT Filed: Dec. 12, 2018

(86) PCT No.: PCT/CN2018/120698
§ 371 (c)(1),
(2) Date: Jun. 24, 2020

(87) PCT Pub. No.: WO2019/128720
PCT Pub. Date: Jul. 4, 2019

(65) Prior Publication Data
US 2020/0323532 A1  Oct. 15, 2020

(30) Foreign Application Priority Data

Dec. 26, 2017 (CN) .......................... 201711431490.0
Dec. 26, 2017 (CN) .......................... 201711451948.9
(Continued)

(51) Int. Cl.
*A61B 17/115* (2006.01)
*A61B 17/326* (2006.01)
*A61B 17/00* (2006.01)

(52) U.S. Cl.
CPC ........ *A61B 17/1155* (2013.01); *A61B 17/326* (2013.01); *A61B 2017/0046* (2013.01);
(Continued)

(58) Field of Classification Search
CPC .. A61B 2017/0046; A61B 2017/00455; A61B 2017/1155; A61B 2017/00862
See application file for complete search history.

(56) References Cited

U.S. PATENT DOCUMENTS 9,603,599 B2 * 3/2017 Miller ................ A61B 17/1155
2017/0181748 A1   6/2017 Hessler et al.

FOREIGN PATENT DOCUMENTS

CN    103142278 A    6/2013
CN    106388948 A    2/2017
(Continued)

OTHER PUBLICATIONS

International Search Report regarding related App. No. PCT/CN2018/120698; dated Feb. 28, 2019.
(Continued)

*Primary Examiner* — Anna K Kinsaul
*Assistant Examiner* — Daniel Jeremy Leeds
(74) *Attorney, Agent, or Firm* — Dickinson Wright PLLC

(57) ABSTRACT

A handle assembly and a stapler including the same are provided. The handle assembly includes: a first handle, a second handle, a sliding slot disposed on the first handle, a slider slidably disposed in the sliding slot, a second indicator and a first indicator connected to a first end of the second indicator; when the first indicator is rotated in a first direction, a second end of the second indicator is driven to rotate in the first direction and the slider is pushed to move from a first section of the sliding slot to a second section of the sliding slot; when the slider is pressed against the second handle due to rotation of the first handle in a second direction, the second handle is linked with the first handle and the second end of the second indicator is pushed by the slider to rotate in the second direction.

19 Claims, 36 Drawing Sheets

(30) Foreign Application Priority Data

Dec. 26, 2017 (CN) .......................... 201721846423.0
Dec. 26, 2017 (CN) .......................... 201721849153.9

(52) U.S. Cl.
CPC ............... *A61B 2017/00367* (2013.01); *A61B 2017/00455* (2013.01); *A61B 2017/00862* (2013.01)

(56) References Cited

FOREIGN PATENT DOCUMENTS

| | | |
|---|---|---|
| CN | 206261635 U | 6/2017 |
| CN | 107106180 A | 8/2017 |
| CN | 107485429 A | 12/2017 |
| EP | 1964523 A1 | 9/2008 |
| EP | 2092898 A2 | 8/2009 |
| JP | 2009189831 A | 8/2009 |
| JP | 2015503949 A | 2/2015 |
| RU | 145252 U1 | 9/2014 |

OTHER PUBLICATIONS

Communication regarding corresponding RU Pat. App. 2020122630/14; dated Nov. 13, 2020.
Communication regarding corresponding JP Pat. App. 2020-554350; dated Jun. 22, 2021.
Extended European Search Report regarding EP App. No. 18895634.6 dated Sep. 29, 2021.

\* cited by examiner

HANDLE ASSEMBLY AND STAPLER INCLUDING THE SAME

CROSS-REFERENCE TO RELATED APPLICATIONS

This application is based upon PTC patent application No. PCT/CN2018/120698, filed on Dec. 12, 2018, which claims priority to Chinese Patent Applications No. 201711431490.0, No. 201721849153.9, No. 201711451948.9 and No. 201721846423.0, filed on Dec. 26, 2017, the entire contents of which are incorporated herein by reference.

TECHNICAL FIELD

The present disclosure relates to the field of medical instrument technology, in particular to the field of stapler technology, and specifically to a handle assembly and a stapler including the same.

BACKGROUND

Digestive tract tumor is one of human diseases of high incidence. During treatment a circular stapler is widely used for suturing physiological tissues such as tissues in the digestive tract, instead of the manual operation by doctors. The circular stapler is a common surgical instrument, and used for suturing from end to end, or from end to side of the physiological tissues of esophagus, stomach, intestine, etc., in a way of axial internal stapling. During the process of anastomoses, two sections of tissues are accommodated in the stapler, and form a circular anastomotic stoma after firing the stapling, to rebuild a tissue channel.

In the prior art, the circular stapler includes an instrument body, a handle assembly movably connected to the instrument body and an anvil assembly cooperated with the instrument body. The instrument body includes a cartridge assembly located on a distal end and a knob located on a proximal end thereof. The cartridge assembly includes a circular cartridge and a cutter, and the knob can be rotated relative to the instrument body. In the present disclosure, the positions of the distal end and the proximal end are defined relative to an operator, wherein, the proximal end is an end closer to the operator, the proximal end is another end far from the operator and closer to a surgical position. The anvil assembly includes an anvil, an anvil cap on the top of the anvil, a cutter anvil inside the anvil and an anvil shaft detachably connected to the instrument body. During operation, after the tumor tissues are separated and removed, the anvil shaft is connected to the distal end of instrument body through a purse on one end of the tissues, the knob is rotated to shorten a distance between the cartridge and the anvil to an appropriate distance. The stapler is then able to be fired by pressing the handle to accomplish the suturing operation. Along with the development of medical instruments, the circular stapler has been more and more widely used for treatment of diseases such as hemorrhoids.

Meanwhile, in urinary surgical field, another kind of circular stapler is also applied to treat redundant prepuce and phimosis, which is called circumcision stapler. The structure of the circumcision stapler is similar to the circular stapler for digestive tract as aforementioned, except for the glans cap assembly cooperated with the instrument body. Similarly, the glans cap assembly includes an anvil, a glans cap fixedly connected to the anvil, a cutter anvil and a central rod detachably connected to the instrument body. During operation, the prepuce tissues to be cut are fixed to the glans cap, the central rod is configured to the distal end of the instrument body, and the knob is rotated to shorten a distance between the glans gap and the cartridge to an appropriate distance. The stapler is then able to be fired by pressing the handle to accomplish the suturing operation.

Along with the technological development, the firing transmission mechanism of the circular stapler has been improved with a lockout mechanism added. Therefore, when the stapler is not ready to be fired, even the doctor presses the handle, the handle cannot be moved for the lockout mechanism, to prevent the stapler from being fired by mistake. However, in practice, the insurance mechanism has some defects. For example, the insurance mechanism has some negative impacts on the operators' experience, and the casing of the stapler may be cracked if the doctor presses the handle vigorously.

SUMMARY

The present disclosure provides a handle assembly and a stapler including the same. When the stapler is not ready to be fired, the first handle and the second handle are not linked, thereby the stapler cannot be fired. The indicator includes two sections, and the indicator will not block the rotation of the handle assembly when the first handle is rotated.

Embodiments of the present disclosure provide a handle assembly for firing a stapler, the handle assembly includes: a first handle and a second handle, wherein, a sliding slot is disposed on the first handle, the sliding slot includes a first section and a second section connected with each other, a slider is slidably disposed in the sliding slot, the first handle and the second handle are not linked when the slider is in the first section of the sliding slot; a first indicator and a second indicator, wherein, the first indicator is connected to a first end of the second indicator, a second end of the second indicator is driven to rotate in a first direction and the slider is pushed to move from the first section of the sliding slot to the second section of the sliding slot, when the first indicator is rotated in the first direction. The second handle is linked with the first handle and the second end of the second indicator is pushed by the slider to rotate in a second direction, when the slider is in the second section of the sliding slot and pressed against the second handle due to rotation of the first handle in the second direction.

In some embodiments, the first indicator and the first end of the second indicator are rotatably connected through an indicator return member, and the indicator return member is deformed when the second end of the second indicator is pushed to rotate in the second direction by the slider.

In some embodiments, the indicator return member includes a third pin and a third torsion spring sleeved on the third pin, the third pin passes through the first end of the second indicator and is fixed to the first indicator, and two ends of the third torsion spring are pressed against the first indicator and the second indicator, respectively.

In some embodiments, a first clamping slot for the third torsion spring is disposed on the first indicator, and a second clamping slot for the third torsion spring is disposed on the first end of the second indicator, and the two ends of the third torsion spring are embedded in the first clamping slot and the second clamping slot, respectively.

In some embodiments, the indicator return member includes a third pin and a tension spring, the third pin passes through the first end of the second indicator and is fixed to the first indicator, and the tension spring is disposed between the first indicator and the second indicator.

In some embodiments, the second indicator is an elastic indicator, and the second indicator is deformed elastically when the second end of the second indicator is pushed to rotate in the second direction by the slider.

In some embodiments, the first indicator and the second indicator are integrally formed.

In some embodiments, the second indicator is made of elastic resin, rubber material or metal material.

In some embodiments, the second end of the second indicator is curved toward a distal end of the stapler relative to the first end of the second indicator, and a smooth transition is configured between the first end and the second end of the second indicator.

In some embodiments, a positioning portion is disposed between two ends of the first indicator, and the first indicator is rotatably connected to a casing of the stapler through the positioning portion.

In some embodiments, a fourth pin passes through the positioning part and a fourth torsion spring is sleeved on the fourth pin, the fourth pin is fixed on the casing of the stapler, and two ends of the fourth torsion spring are pressed against the casing of the stapler and the first indicator, respectively.

In some embodiments, a projecting portion is disposed between the first end of the first indicator and the positioning portion, a second end of the first indicator is connected to the first end of the second indicator, the projecting portion is located correspondingly to a position of a pulling hook of a pulling sheet, a proximal end of the pulling sheet is sleeved on a screw rod, and a distal end of the screw rod is provided with a knob, when rotating the knob, the pulling sheet is driven to move toward a proximal end of the stapler, and the first indicator is pulled, by the pulling sheet and through the projecting portion, to rotate in the first direction; the first handle or the second handle includes a pulling sheet contact portion, the pulling sheet contact portion is pressed against the pulling sheet, making the pulling hook of the pulling sheet separated from the indicator, when the first handle and the second handle are rotated in the second direction.

In some embodiments, a slider return spring is disposed on the first handle, the slider return spring is in a deformation state by a force exerted by the slider, when the slider is in the second section of the sliding slot; and the slider is driven to move from the second section to the first section of the sliding slot, when the slider return spring restores from the deformation state to an initial state.

In some embodiments, the first indicator and the first end of the second indicator are rotatably connected through an indicator return member; a force exerted on the slider by the slider return spring is less than a force exerted on the indicator by the indicator return member, when the slider is in the second section of the sliding slot, and the second handle has not been pressed against the slider while the first handle rotating in the second direction.

In some embodiments, the second indicator is an elastic indicator; a force exerted on the slider by the slider return spring is less than a force formed by the second indicator resisting elastic deformation, when the slider is in the second section of the sliding slot, and the second handle has not been pressed against the slider while the first handle rotating in the second direction.

In some embodiments, the handle assembly further includes: a first torsion spring and a first pin, wherein, the first pin passes through the first handle and the second handle, and is fixed to a casing of the stapler, the first torsion spring is sleeved on the first pin, and two ends of the first torsion spring are pressed against the casing of the stapler and the second handle, respectively; and a second torsion spring and a second pin, wherein, the second pin is fixed to the casing of the stapler, the second torsion spring is sleeved on the second pin, and two ends of the second torsion spring are pressed against the casing of the stapler and the first handle, respectively.

In some embodiments, the handle assembly further includes: a first torsion spring and a first pin, wherein, the first pin passes through the first handle and the second handle, and is fixed to a casing of the stapler, the first torsion spring is sleeved on the first pin, and two ends of the first torsion spring are pressed against the casing of the stapler and the second handle, respectively; and a handle return pressure spring connected between the first handle and the casing of the stapler.

In some embodiments, the handle assembly further includes: a first torsion spring and a first pin, wherein, the first pin is fixed to the second handle and passes through the first handle, the first torsion spring is sleeved on the first pin, and two ends of the first torsion spring are pressed against the first handle and the second handle, respectively; and a second torsion spring and a second pin, wherein, the second pin is fixed to a casing of the stapler and passes through the second handle, the second torsion spring is sleeved on the second pin, and two ends of the second torsion spring are pressed against the second handle and the casing of the stapler, respectively.

The embodiments of the present disclosure further provide a stapler including the handle assembly.

The handle assembly and the stapler including the same provided by the present disclosure have the following advantages.

The present disclosure provides a handle assembly and a stapler including the same, the handle assembly includes the first handle and the second handle, and only the movement of the second handle can fire the stapler to perform cutting and suturing actions. During operation, the first handle can be pressed by the doctor whether the stapler is ready to be fired or not. When the stapler is not ready to be fired, the second handle cannot be actuated by the first handle and the stapler cannot be fired. The indicator includes the first indicator and the second indicator, and the second indicator can be pushed to rotate by the slider when the first handle and the second handle are rotated together. Therefore, the indicator will not block the rotation of the handle assembly, which ensures smooth movement of the stapler when the stapler is fired and improves user experience.

BRIEF DESCRIPTION OF THE DRAWINGS

Embodiments of the present disclosure will now be described, by way of example only, with reference to the accompanying schematic drawings, and the other technical features, objects and advantages will be more obvious.

DETAILED DESCRIPTION

Figure 1:
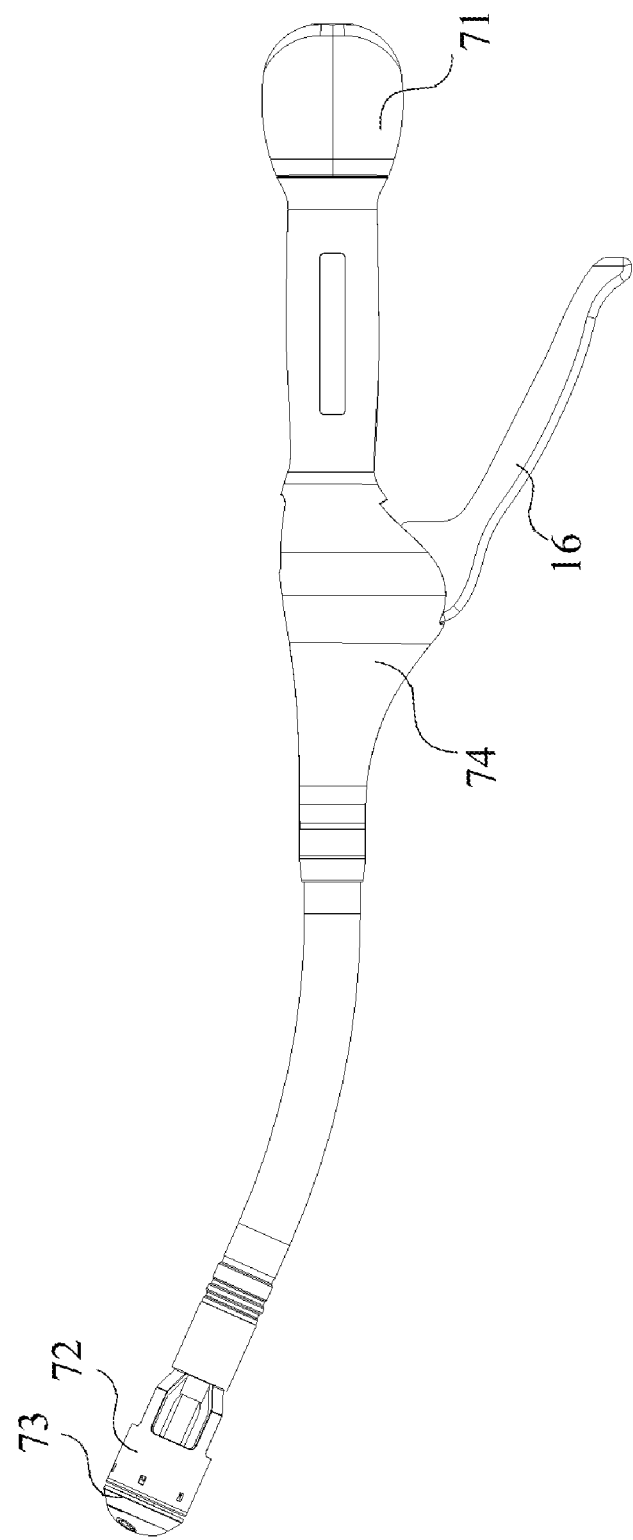
FIG. 1 is a schematic view of a handle assembly applied in a stapler according to a first embodiment of the present disclosure.
Figure 2:
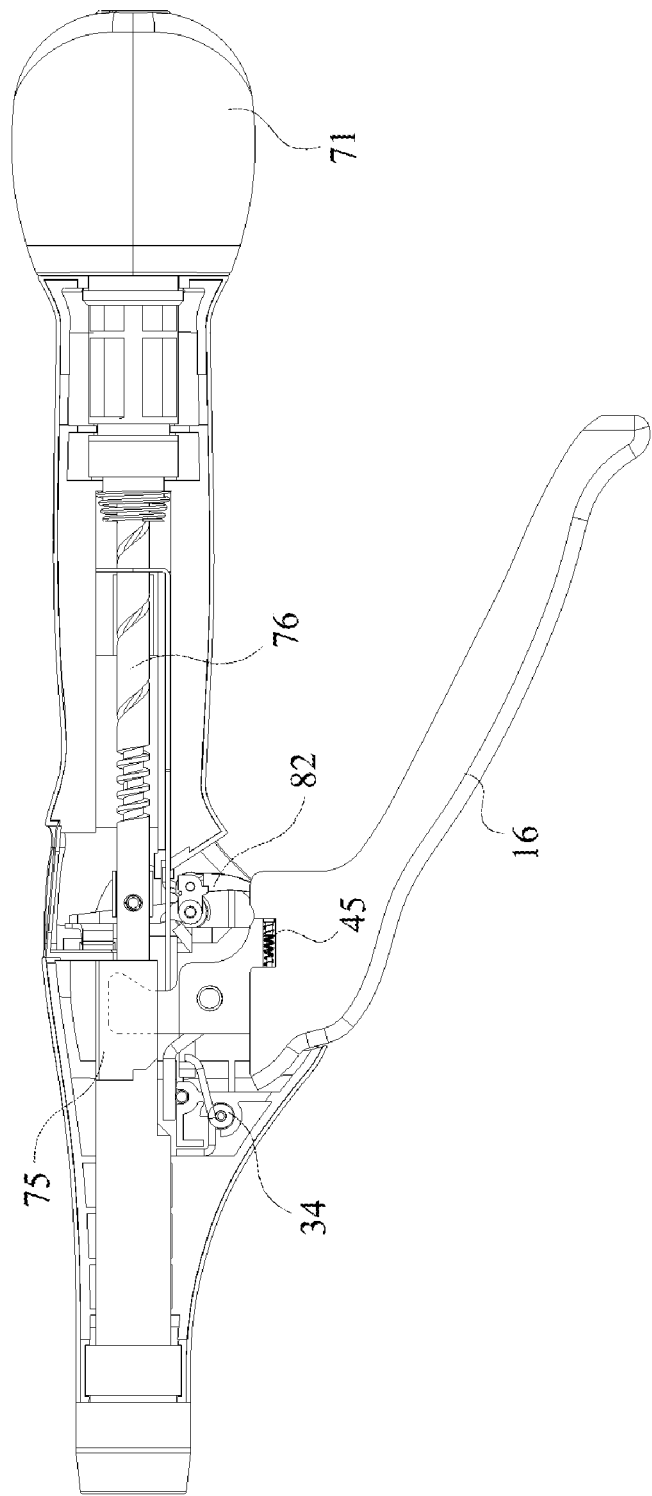
FIG. 2 is a schematic view of the handle assembly applied in a conventional circular stapler according to the first embodiment of the present disclosure.

In the following, embodiments of the present disclosure will be described in detail with reference to the figures. The concept of the present disclosure can be implemented in a plurality of forms, and should not be understood to be limited to the embodiments described hereafter. In contrary, these embodiments are provided to make the present disclosure more comprehensive and understandable, and so the conception of the embodiments can be conveyed to those skilled in the art fully. Same reference signs in the figures refer to same or similar elements, so repeated description of them will be omitted.

In order to solve the technical problems in the prior art, the present disclosure provides a handle assembly for firing a stapler, wherein the handle assembly includes a first handle and a second handle, wherein, the first handle is provided with a sliding slot, the sliding slot includes a first section and a second section connected with each other, a slider is slidably disposed in the sliding slot, the first handle and the second handle are not linked when the slider is in the first section of the sliding slot; a first indicator and a second indicator, wherein, the first indicator is connected to a first end of the second indicator; a second end of the second indicator is driven to rotate in a first direction and the slider is pushed to move from the first section of the sliding slot to the second section of the sliding slot, when the first indicator is rotated in the first direction; the second handle is linked with the first handle, and the second end of the indicator is pushed by the slider to rotate in a second direction, when the slider is in the second section of the sliding slot, and the first handle is rotated in a second direction until the slider is pressed against the second handle.

Therefore, by adopting the present disclosure, the doctor can press the first handle regardless of whether the stapler is ready to be fired or not during operation. However, the second handle cannot be actuated by the first handle and the stapler cannot be fired, when the stapler is not ready to be fired. The indicator is divided into the first indicator and the second indicator, and the second indicator can be pushed by the slider to rotate when the first handle and the second handle are rotated together. Therefore, the indicator will not block the rotation of the handle assembly, which ensures smooth movement of the stapler when the stapler is fired.

In addition, a reset mechanism can be further provided for the second indicator. During firing, the second indicator is pushed by the slider to rotate, and after the firing is completed, the second indicator can return to an initial position under a reset action of the reset mechanism. The structure of the handle assembly and the stapler of the present disclosure will be specifically described below with reference to two embodiments. Wherein, the two embodiments use two different reset mechanisms, an indicator return member and an elastic indicator, respectively. The present disclosure is not limited to this, and other reset mechanisms are also possible.

FIG. 1 shows the structure of the stapler according to a first embodiment of the present disclosure. A cartridge assembly 72 and an anvil assembly 73 are disposed at a distal end of the stapler, a knob 71 and the handle assembly are disposed at a proximal end of the stapler, and a handle casing 16 is disposed outside the handle assembly. The stapler can be fired by pressing the handle assembly.

FIGS. 2 to 9 show the structure of the handle assembly in the initial state in an embodiment of the present disclosure, wherein part of the casing or part of the assembly has been omitted, in order to clearly show the structure of the handle assembly and the cooperation of the handle assembly and other parts. In order to achieve the object mentioned above, the handle assembly of the present disclosure is divided into the first handle 1 and the second handle 2, and the stapler can be fired only when the second handle 2 is rotated. A first pin 31 passes through the first handle 1 and the second handle 2, simultaneously, the first pin 31 is fixed to the casing 74 of the stapler, and a first torsion spring 32 is sleeved on the first pin 31. Both ends of the first torsion spring 32 are pressed against the casing 74 of the stapler and the second handle 2, respectively. After the second handle 2 is rotated, the second handle 2 can be reset when external force is released.

In addition, a second torsion spring 34 and a second pin 33 are disposed for resetting the first handle 1. The second pin 33 is fixed to the casing 74 of the stapler, the second torsion spring 34 is sleeved on the second pin 33, and both ends of the second torsion spring 34 are pressed against the casing 74 of the stapler and the first handle 1, respectively.

In order to realize linkage of the first handle 1 and the second handle 2, a sliding slot 41 and a slider 42 are disposed on the first handle 1, the sliding slot 41 includes a first section 411 and a second section 412 connected to each other, and the second handle 2 includes a handle contact portion 25. When the slider 42 is in the first section 411 of the sliding slot 41, and the first handle 1 is pressed to rotate in the second direction, the slider 42 is not pressed against the handle contact portion 25, and the second handle 2 is in an insurance position, that is, although the first handle 1 is rotated, it cannot fire the stapler and is in an invalid state. In this embodiment, the second direction is a counterclockwise direction shown in FIGS, but the present disclosure is not limited to this. Therefore, when the doctor presses the first handle 1, the first handle 1 can be easily rotated, while the second handle 2 will not be triggered. At the same time, the force of pressing the first handle 1 is very small since the stapler is in an invalid firing state right now. The doctor can also know through his operation experience that the stapler is currently not fired, and the casing of the stapler will not be cracked.

When the slider 42 is in the second section 412 of the sliding slot 41, and the first handle 1 is held to rotate in the counterclockwise direction, the slider 42 is pressed against the handle contact portion 25 and the second handle 2 is actuated to rotate from the insurance position to a firing position. When the second handle 2 is rotated in the counterclockwise direction, a staple pushing rod 75 will be pushed to move toward the distal end of the stapler, thereby the stapler will be fired.

It should be noted that the first section 411 and the second section 412 of the sliding slot 41 in the present disclosure are relative concepts, which not necessarily mean the two ends of the sliding slot 41. In the view shown in FIGS, the first section 411 is located on the right side of the second section 412 of the sliding slot 41. Holding the first handle 1, the relation between the slider 42 and the handle contact portion 25 will be different, when the slider 42 is in the first section 411 and the second section 412 of the sliding slot 41. The slider 42 will not interfere with the handle contact portion 25 when located in the first section 411 of the sliding slot 41, and the slider 42 will interfere with the handle contact portion 25 when located in the second section 412 of the sliding slot 41.

In order to realize the sliding of the slider 42 in the sliding slot 41, the handle assembly of the embodiment further includes an indicator. In this embodiment, the indicator includes a first indicator 81 and a second indicator 82, the first indicator 81 and a first end 821 of the second indicator 82 are rotatably connected through an indicator return member. When a first end 811 of the first indicator 81 is rotated in the first direction from a first position area to a second position area, a second end 822 of the second indicator 82 is driven to rotate clockwise, and the slider 42 is pushed to move from the first section 411 of the sliding slot 41 to the second section 412 of the sliding slot 41. In this embodiment, the first direction is the clockwise direction shown in FIGS, but the present disclosure is not limited to this. The body portion of the stapler is provided with a window, the window is located correspondingly to the first position area and the second position area and used for observing the position of the first end 811 of the first indicator 81 during operation. The stapler is in the insurance state and cannot be fired when the first end 811 of the first indicator 81 is in the first position area, and the stapler can be fired when the first end 811 of the first indicator 81 is in the second position area. To give the doctor a more obvious indication, the area on the window corresponding to the second position area indicating the stapler being ready to be fired is colored green.

Figure 3:
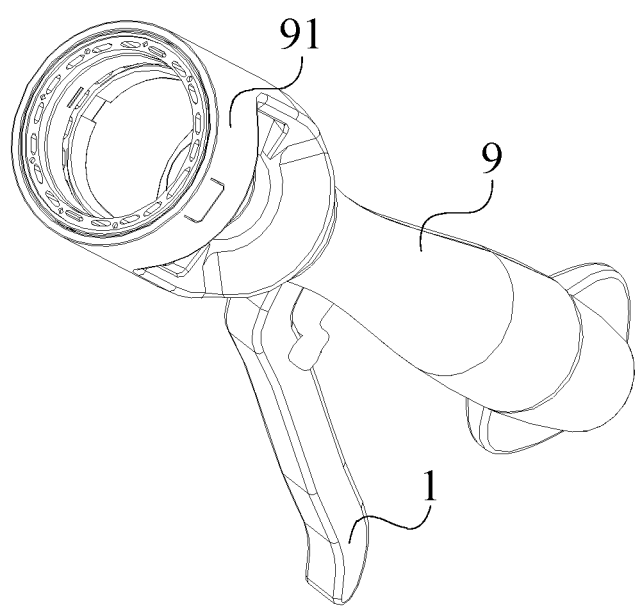
FIG. 3 is a schematic view of the handle assembly applied in a circumcision stapler according to the first embodiment of the present disclosure.
Figure 4:
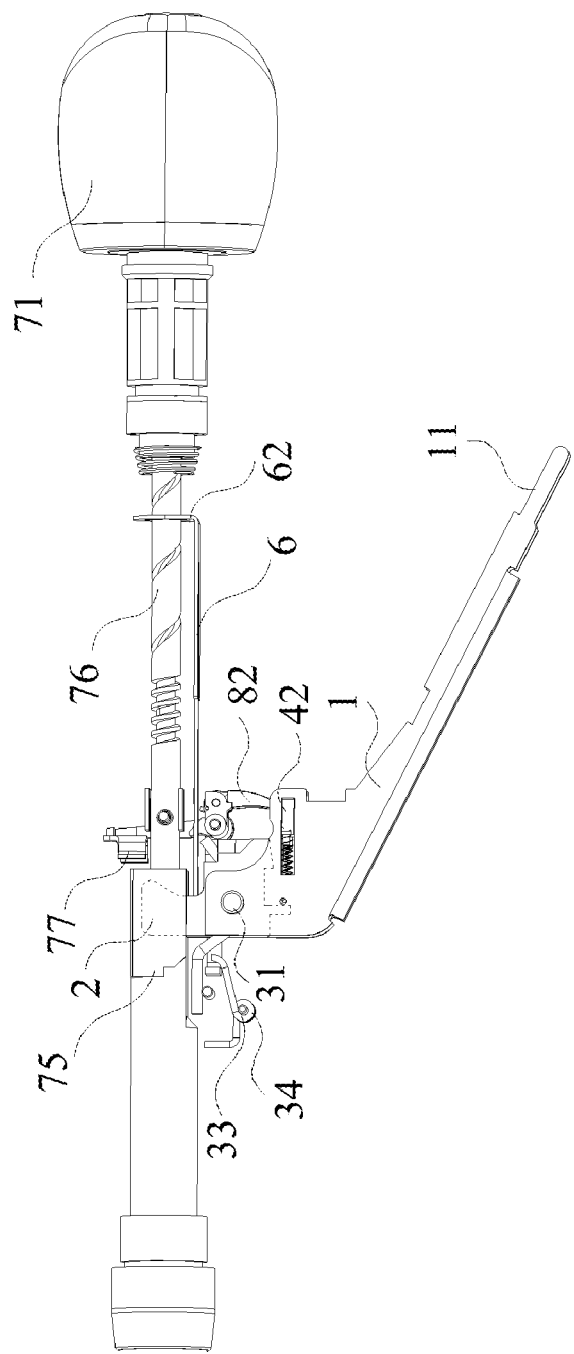
FIG. 4 is a schematic view of the handle assembly in an initial state according to the first embodiment of the present disclosure.
Figure 5:
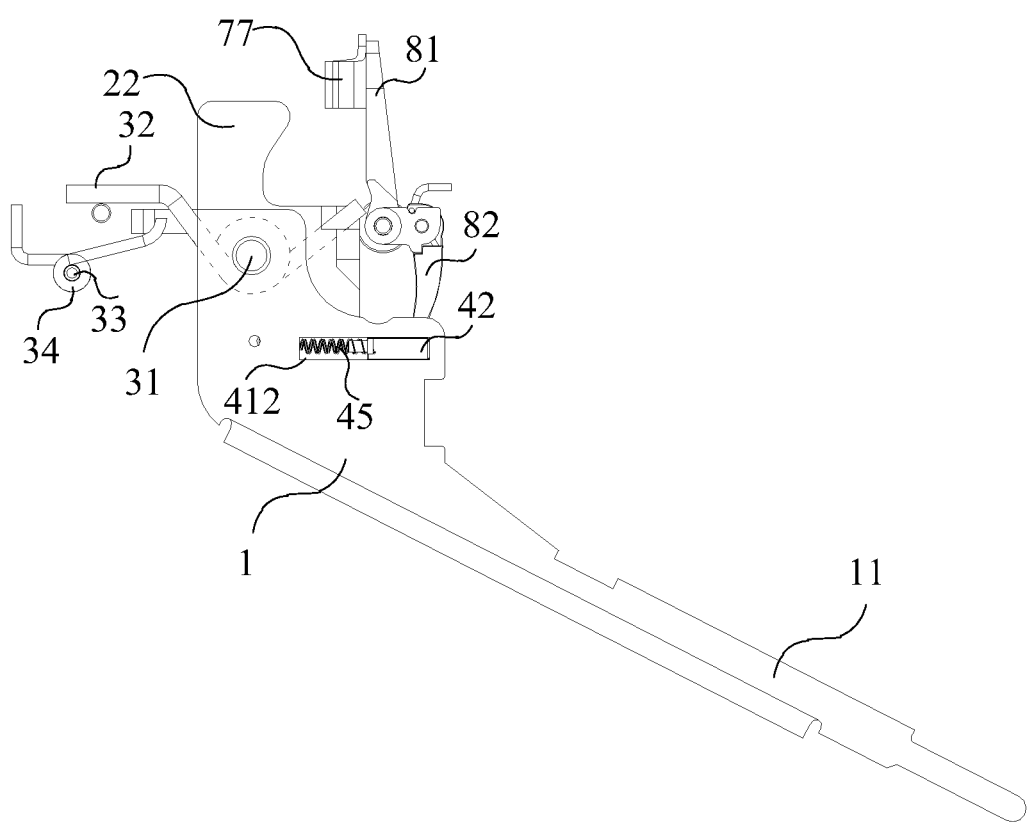
FIG. 5 is a schematic view of the handle assembly in an initial state according to the first embodiment of the present disclosure.
Figure 6:
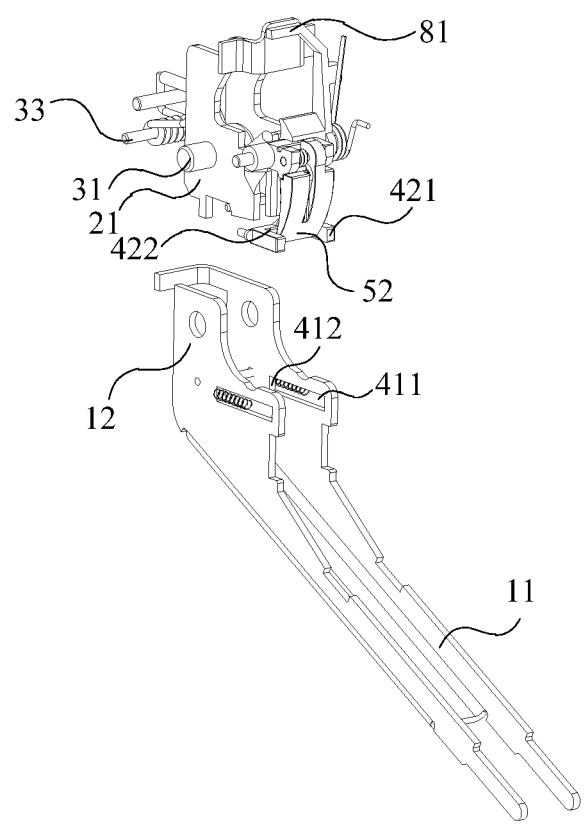
FIG. 6 is a schematic view of the handle assembly in an initial state according to the first embodiment of the present disclosure.
Figure 7:
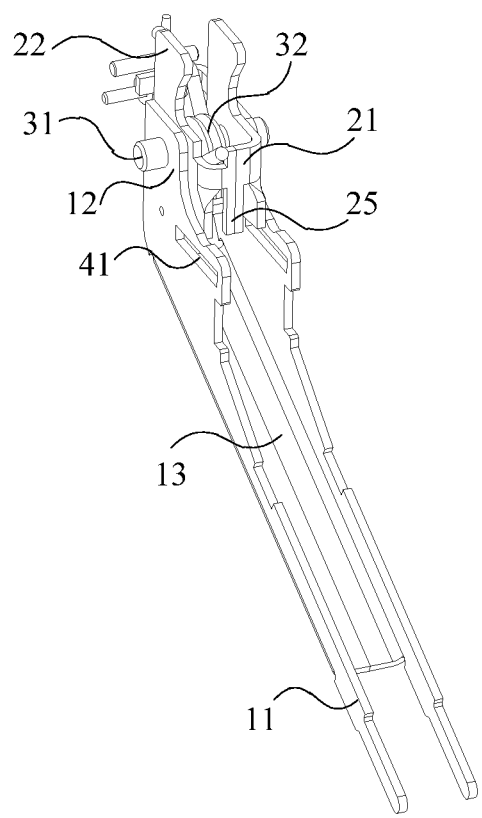
FIG. 7 is a schematic view of the handle assembly in an initial state according to the first embodiment of the present disclosure.
Figure 8:
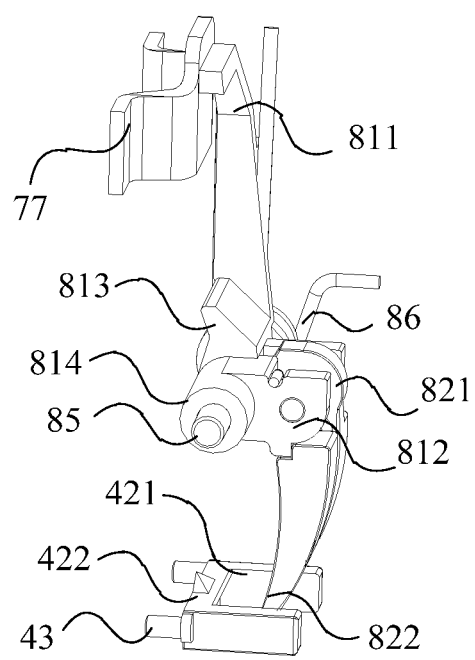
FIG. 8 is a schematic view of the handle assembly in an initial state according to the first embodiment of the present disclosure.
Figure 9:
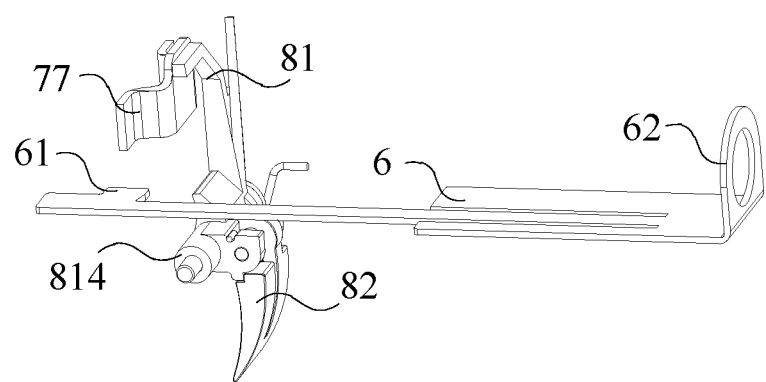
FIG. 9 is a schematic view of the handle assembly in an initial state according to the first embodiment of the present disclosure.

The present disclosure can be applied not only to the conventional circular stapler, but also to the circumcision stapler. For example, as shown in FIG. 3, the structure of body portion of the circumcision stapler 9 to which the handle assembly is applied. A cartridge assembly 91 and a glans cap assembly (not shown in FIG. 3) cooperated with the cartridge assembly 9 are disposed at a distal end of the body portion of the circumcision stapler 9. When using the circumcision stapler, the second handle 2 is movably connected to one end of the circumcision stapler, and the second end of the second handle 2 is cooperated with a staple pushing component of the circumcision stapler. When a firing condition is met, the staple pushing component will be pushed by the second handle 2 and the circumcision stapler will be fired.

Figure 10:
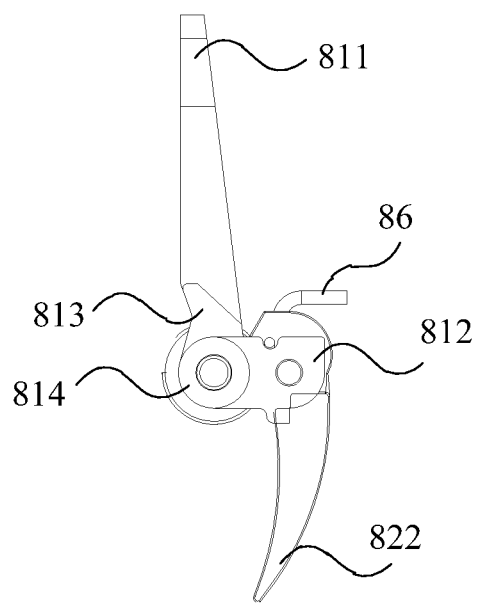
FIG. 10 is a front view of an indicator according to the first embodiment of the present disclosure.
Figure 11:
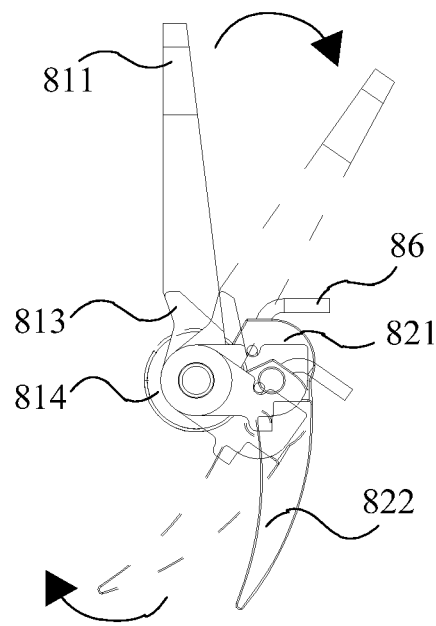
FIG. 11 is a schematic view of the indicator rotating in a first direction according to the first embodiment of the present disclosure.
Figure 12:
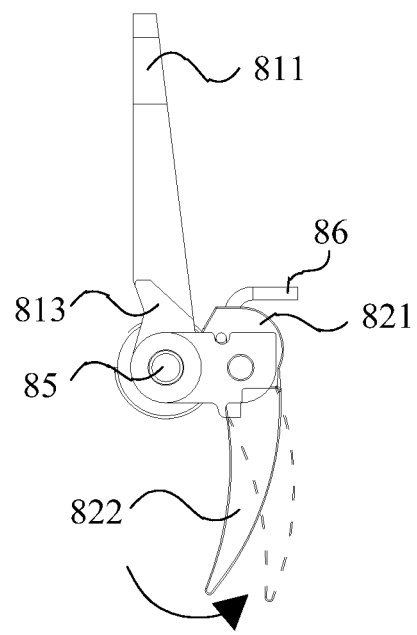
FIG. 12 is a schematic view of a second indicator rotating in a second direction according to the first embodiment of the present disclosure.

FIGS. 10 to 12 show the structure of the indicator in different states. The function of the indicator return member is to ensure that the second indicator 82 can be driven to rotate clockwise, simultaneously, when the first indicator 81 is rotated clockwise, that is, the indicator can be rotated to a position shown in broken lines in FIG. 11. The second indicator 82 will be rotated counterclockwise relative to the first indicator 81 when the second end 822 of the second indicator 82 receives a rightward force, that is, the second indicator 82 can be rotated to a position shown in broken lines in FIG. 12. After the rightward force is released, the second indicator 82 can return to the initial position shown in solid lines by the restoring force of the indicator return member. Therefore, the indicator will not block the movement path of the slider 42 when the first handle 1 and the second handle 2 are rotated in linkage. When the slider 42 is in the second section 412 of the sliding slot 41 and the first handle 1 is rotated counterclockwise, the slider 42 is rotated accordingly. At this time, the indicator still has a leftward force on the slider 42 and the slider 42 will avoid the indicator. As the first handle 1 continues to rotate, after the slider 42 is pressed against the handle contact portion 25, the slider 42 is blocked by the second handle 2 and cannot continue to avoid the indicator. If the indicator is an un-deformable integral indicator, the movement path of the slider 42 will be blocked by the indicator, the rotating and firing process of the second handle 2 is not smooth, and the user experience is not good.

Therefore, the present disclosure divides the indicator into two parts: the first indicator 81 and the second indicator 82. When the slider 42 cannot continue to avoid the indicator, the second indicator 82 will rotate counterclockwise to avoid the slider 42 under an action of the slider 42, the rotation process will make the indicator return member deformed. After the first handle 1 is released, the second indicator 82 can rotate clockwise and back to the initial position under the restoration effect of the indicator return member. Therefore, the structure is adopted to solve the problem caused by the integral indicator that the handle movement is not smooth when the stapler is fired. The firing of the second handle 2 will not be affected wherever the indicator is. The indicator is allowed to interference with other components when designing the stapler, therefore, a more compact structure of the stapler can be achieved.

Figure 13:
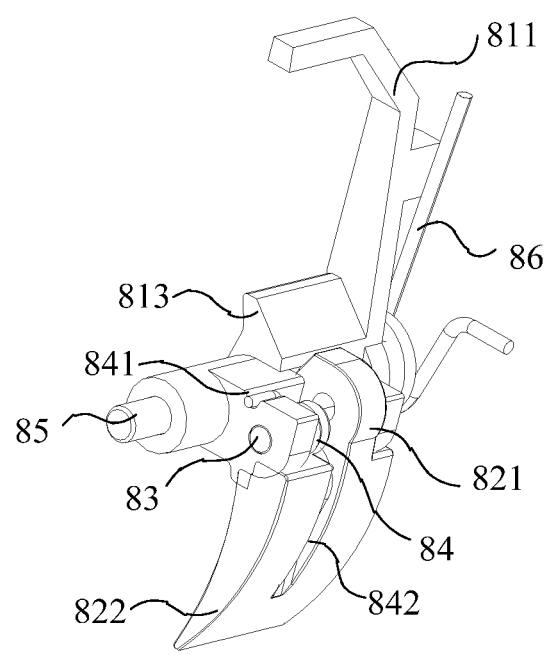
FIG. 13 is a perspective view of the indicator according to the first embodiment of the present disclosure.
Figure 14:
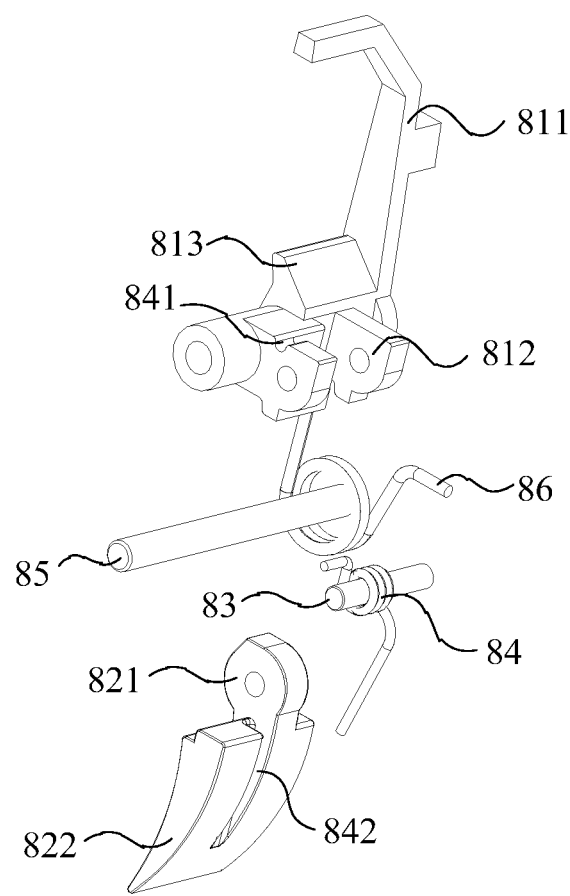
FIG. 14 is an exploded view of the indicator according to the first embodiment of the present disclosure.

FIGS. 13 and 14 show the specific structure of an indicator according to the first embodiment. The first indicator 81 includes a first end 811, a projecting portion 813, a positioning portion 814 and a second end 812. The projecting portion 813 is located correspondingly to a position of a pulling hook 61 of a pulling sheet 6, and the projecting portion 814 is rotatably fixed to the casing 74 of the stapler. A tail portion 62 of the pulling sheet 6 is fixed to a screw rod 76 and will move with the movement of the screw rod 76. When the knob 71 is rotated in a certain direction, the screw rod 76 will move toward the proximal end of the stapler and drive the pulling sheet 6 to move toward the proximal end of the stapler. Meanwhile, the first indicator 81 will be driven, by the pulling hook 61 of the pulling sheet 6 and via the projecting portion 813, to rotate clockwise, thereby the second indicator 82 is also rotated, and the slider 42 is driven to move from the first section 411 of the sliding slot 41 to the second section 412 of the sliding slot 41.

In this embodiment, the indicator return member includes a third pin 83 and a third torsion spring 84 sleeved outside the third pin 83. The third pin 83 passes through the first end 821 of the second indicator 82 and is fixed to the first indicator 81. The first indicator 81 is provided with a first clamping slot 841 for the third torsion spring 84, the first end 821 of the second indicator 82 is provided with a second clamping slot 842 for the third torsion spring 84, and both ends of the third torsion spring 84 are embedded in the first clamping slot 841 and the second clamping slot 842.

A fourth pin 85 passes through the positioning portion 814, a fourth torsion spring 86 is sleeved on the fourth pin 85 and fixed to the casing 74 of the stapler, and both ends of the fourth torsion spring 86 are pressed against the casing 74 of the stapler and the first indicator 81, respectively. Therefore, the first indicator 81 can be rotated around the fourth pin 84 when receives an external force, and can be restored to the initial position via the fourth torsion spring 86 when the external force is released.

In this embodiment, the second end 822 of the second indicator 82 is curved toward the distal end of the stapler relative to the first end 821 of the second indicator 82, a smooth transition is configured between the first end 821 and the second end 822 of the second indicator 82, to form a smooth arc profile, which is conducive to a smoother relative movement when the second end 822 of the second indicator 82 moves to avoid the slider 42, and the second indicator 82 adopts a thin sheet member, therefore to meet the design and use requirements in a narrow space inside the stapler.

In this embodiment, the first handle 1 includes a first cavity 13 having two side walls, the two side walls of the first cavity 13 are respectively provided with two sliding slots 41, and the slider 42 includes two sliding portions 421 and a contact portion 422 in between. The two sliding portions 421 are slidably disposed in the two sliding slots 41, respectively. A handle casing 16 is provided outside the first handle 1, and two grooves are also provided at positions of the handle casing 16 corresponding to the sliding slots 41, a first end and a second end of each groove correspond to the first section 411 and the second section 412 of the sliding slot 41, respectively. In order to realize the limit of the slider 42 after movement, a first limiting member 43 is disposed on each sliding portion 421, a second limiting member is disposed on the second end of each groove, and a return pressure spring 45 for the slider is disposed between each first limiting member 43 and the corresponding second limiting member, respectively. When the slider 42 moves toward the first end 411 of the sliding slot 41, the slider 42 applies a pressing force on the return pressure spring 45 and the return pressure spring 45 will be deformed.

Figure 15:
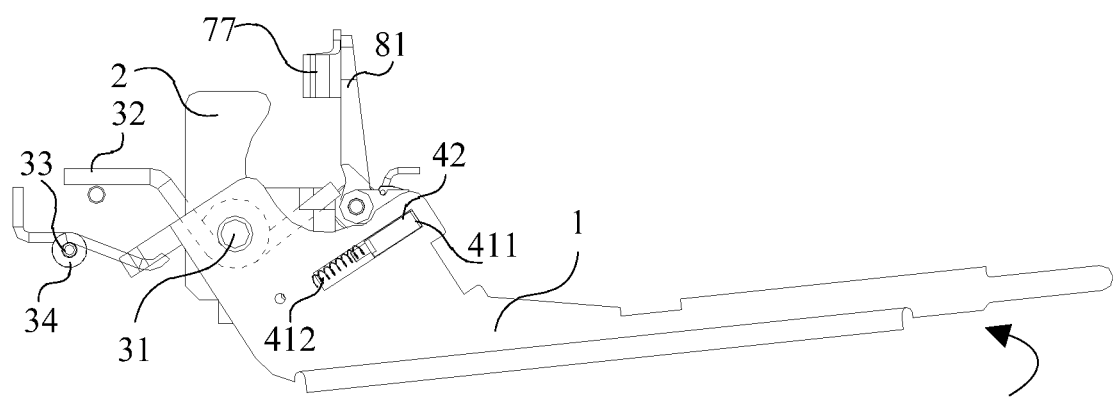
FIG. 15 is a schematic view of the handle assembly in an invalid state according to the first embodiment of the present disclosure.
Figure 16:
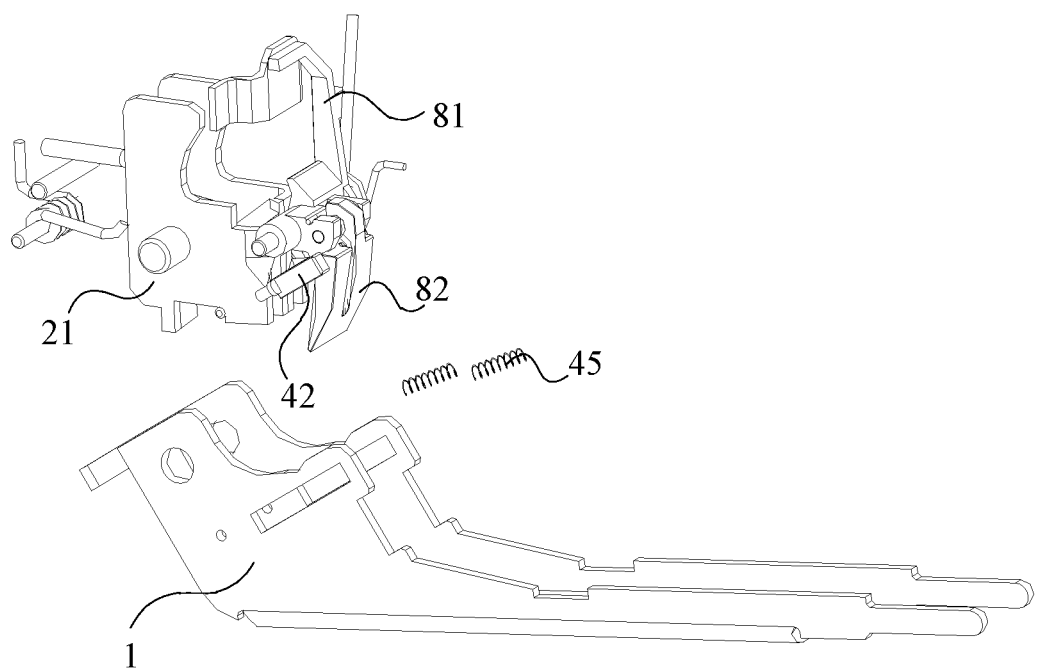
FIG. 16 is a schematic view of the handle assembly in an invalid state according to the first embodiment of the present disclosure.
Figure 17:
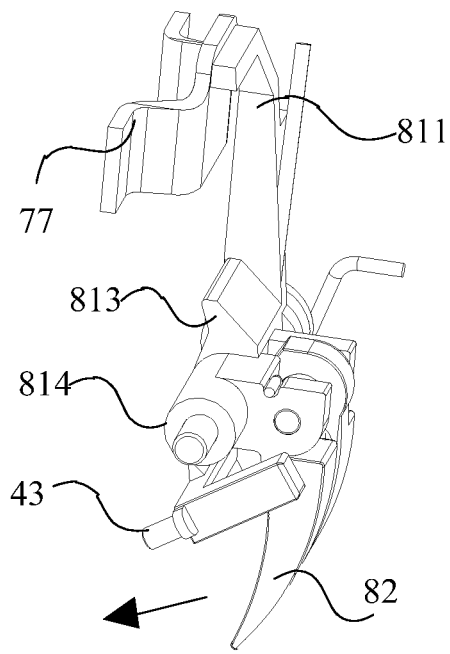
FIG. 17 is a schematic view of the handle assembly in an invalid state according to the first embodiment of the present disclosure.
Figure 18:
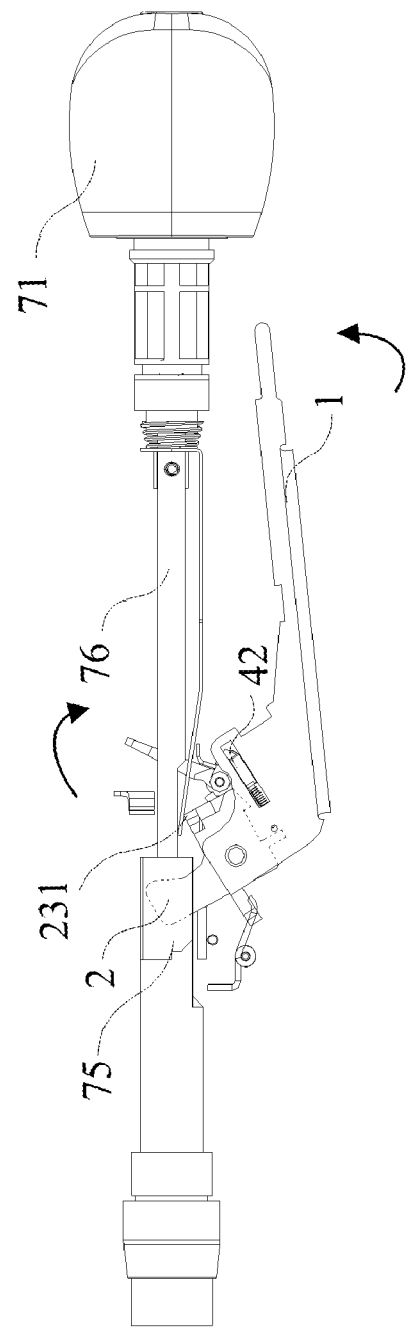
FIG. 18 is a schematic view of the handle assembly in a firing state according to the first embodiment of the present disclosure.
Figure 19:
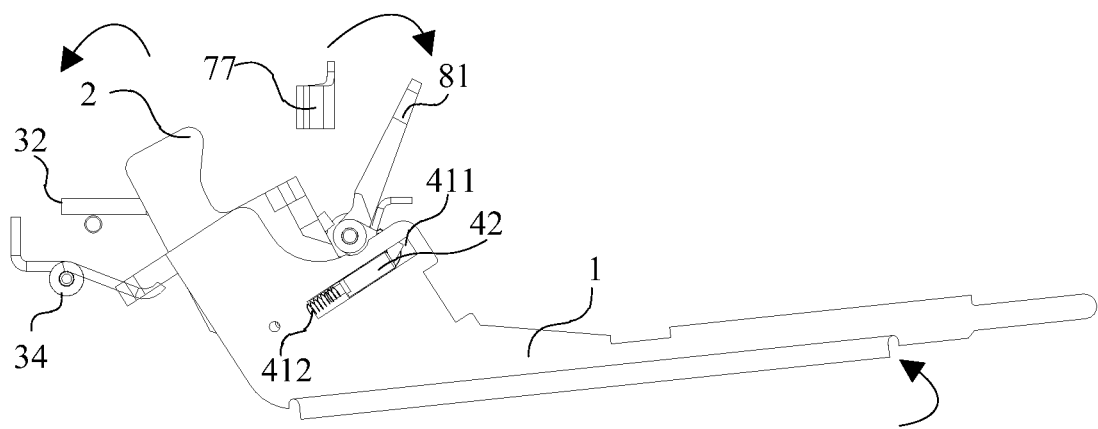
FIG. 19 is a schematic view of the handle assembly in a firing state according to the first embodiment of the present disclosure.
Figure 20:
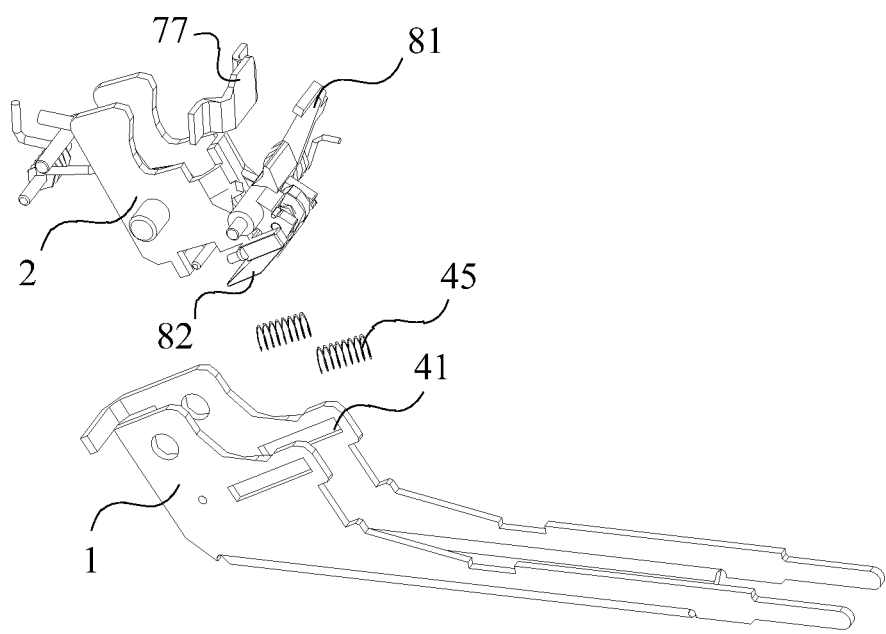
FIG. 20 is a schematic view of the handle assembly in a firing state according to the first embodiment of the present disclosure.

FIGS. 15 to 17 show the structure of the handle assembly in the invalid state according to the first embodiment. In the invalid state, the position of the first indicator 81 does not change, since the first indicator 81 has not been pushed by the pulling sheet 6, the first end 811 of the first indicator 81 is in the first position area, and the second indicator 82 has no force on the slider 42. The slider 42 is still in the first section 411 of the sliding slot 41, the slider 42 and the handle contact portion 25 of the second handle 2 do not interfere on the rotation path of the first handle 1. It should be noted that, when in the initial position, the slider 42 is located at an end of the first section away from the second section of the sliding slot 41, which is the right end in FIGS, under the action of the return pressure spring 45. Of course, the second end 822 of the second indicator 82 may also limit the initial position of the slider 42. In this embodiment, the first end 11 of the first handle 1 is a gripping portion, and the second end 12 includes a connecting portion. The first end 21 of the second handle 2 is located inside a cavity of the connecting portion, and the second end 22 is pressed against the staple pushing rod 75. At this time, the stapler is in an insurance state. Since the torsion force of the second torsion spring 34 is much smaller than the firing force, the first handle 1 can be rotated counterclockwise around the first pin 31 when receives a small holding force from the operator, and the second handle 2 continues to enter into a cavity of the first handle 1, that is, the first handle 1 and the second handle 2 are in an unlinked state, and the second handle 2 does not rotate. When the operator presses the first handle 1, the first handle 1 can be easily rotated, but the second handle 2 is not driven to rotate, and the stapler cannot be fired. The operator can also get tactile feedback at this time, knowing that the first indicator 81 has currently not reached the position indicating the stapler being ready to be fired, and the stapler is not fired. When the external force is released, the first handle 1 will be reset under the action of the second torsion spring 34.

At the same time, as shown in FIG. 17, although the slider 42 is pressed against the second indicator 82, the slider 42 can be pushed by the indicator 82 to move a small displacement in a direction along the arrow shown in FIG. 17, to avoid the indicator, since the force of the return pressure spring 45 is smaller than the force of the indicator return member on the second indicator 82.

FIGS. 18 to 21 show the structure of the handle assembly in the firing state according to the first embodiment. In this process, rotating the knob 71, the pulling sheet 6 is driven by the screw rod 76 to move toward the proximal end of the stapler, and the first indicator 81 is driven to move in the clockwise direction to the second position area, therefore, the slider 42 is pushed by the second indicator 82 to move to the second section 412 of the sliding slot 41 until interfere with the handle contact portion 25. When the first handle 1 is held to rotate counterclockwise, the slider 42 is pressed against the handle contact portion 25 and blocks the second handle 2 from continuing to enter the internal cavity of the first handle 1. As a result, the second handle 2 and the first handle 1 become linked. The second handle 2 is rotated counterclockwise along with the first handle 1, the staple pushing rod 75 is pushed by the second end 22 of the second handle 2, and the staple pushing rod 75 will further push the stapler pushing sheet and the circular cutter of the stapler, to suture and cut the tissues to be operated.

Figure 21:
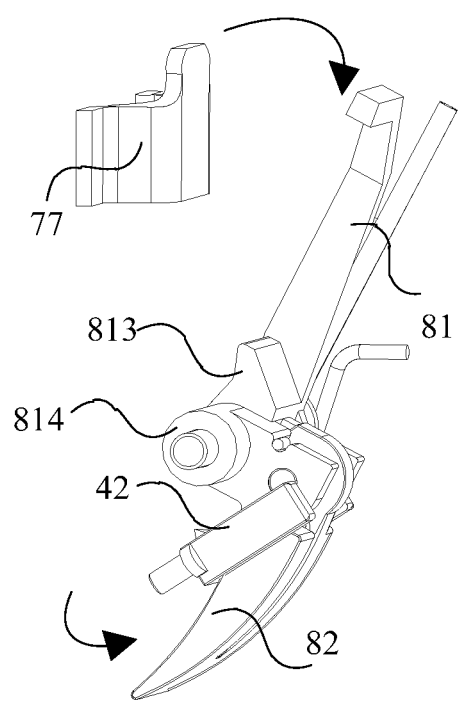
FIG. 21 is a schematic view of the handle assembly in a firing state according to the first embodiment of the present disclosure.
Figure 22:
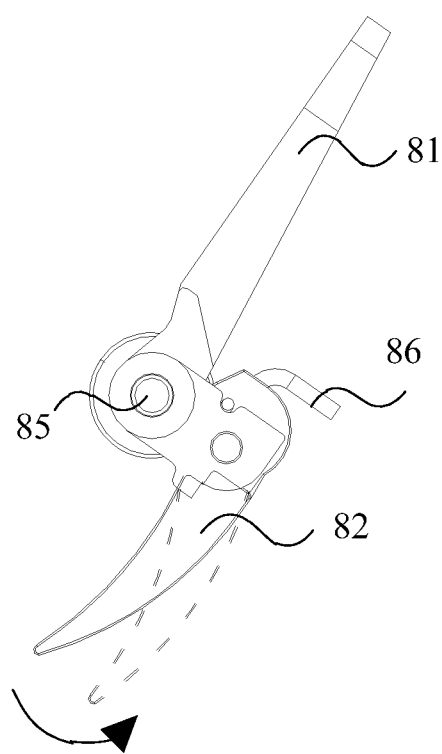
FIG. 22 is a schematic view of a slider pushing the second indicator to rotate when the handle assembly is in the firing state according to the first embodiment of the present disclosure.

The return pressure spring 45 for the slider is further compressed during the movement of the slider 42. The rotation process of the first handle 1 is divided into two steps: firstly, when the slider 42 is not pressed against the second handle 2, the slider 42 will avoid the second indicator 82 since the force exerted by the third torsion spring 84 on the second indicator 82 is much greater than the force exerted by the return pressure spring 45 on the slider 42; secondly, after the slider 42 is pressed against the second handle 2, the slider 42 cannot continue to avoid the second indicator 82 due to the force between the second handle 2 and the first handle 1, therefore, the second indicator 82 will be pushed to rotate counterclockwise to avoid the slider 42. The movement trajectory of the second indicator 82 is shown in FIGS. 21 and 22. After firing the stapler, the operator releases the first handle 1, the slider 42 will be pushed to slide toward the first section 411 of the sliding slot 41 and return to the initial position, under the deformation force of the return pressure spring 45 returning to the initial state. The second indicator 82 will also be rotated clockwise and restored, under the force of the third torsion spring 84.

Figure 23:
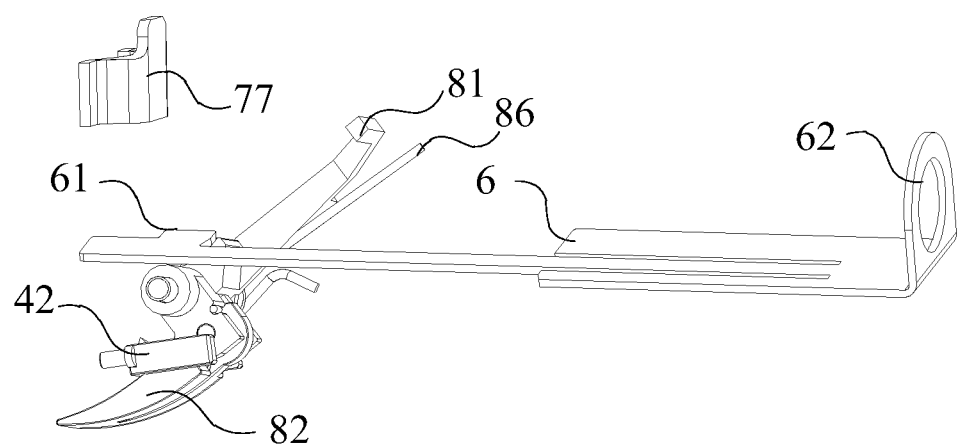
FIG. 23 is a schematic view of a pulling sheet pulling the first indicator to rotate according to the first embodiment of the present disclosure.
Figure 24:
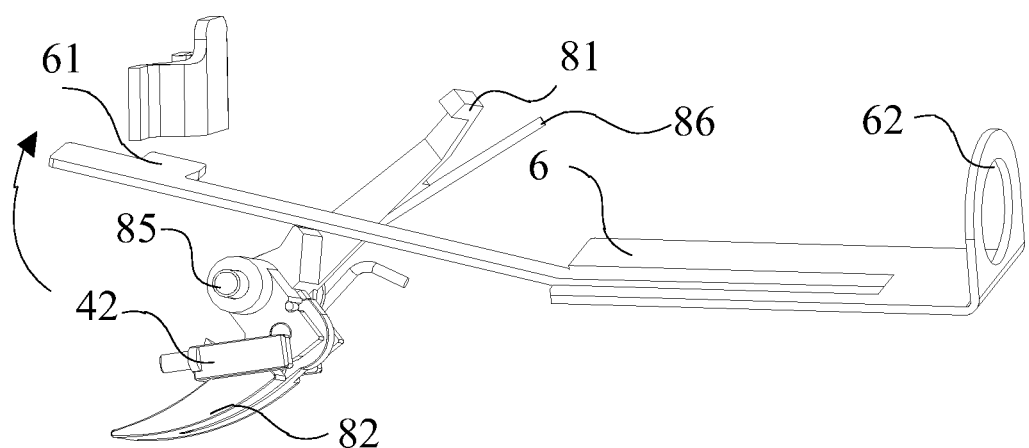
FIG. 24 is a schematic view of the pulling sheet being ejected to disengage from the indicator according to the first embodiment of the present disclosure.

The reset process of the first indicator 81 can be seen in FIGS. 23 and 24. In FIG. 23, the pulling hook 61 is in contact with the projecting portion 813 and can drive the first indicator 81 to rotate clockwise. The second handle 2 is further provided with a pulling sheet contact portion 23. When the second handle 2 is rotated from the insurance position to the firing position, the pulling sheet 6 will be ejected by the pulling sheet contact portion 23 at an ejection point 231, so that the pulling hook 61 of the pulling sheet 6 will be separated from the projecting portion 813. The separation state can be seen in FIG. 24. At this time, the first indicator 81 will automatically return to the initial position under the action of the fourth torsion spring 86. The second end 52 of the indicator 5 is separated from the slider 42, since the first end 51 of the indicator 5 returns to the first position area. After the pushing force of the indicator 8 is released, the slider 42 will return to the first section 411 of the sliding slot 41 under the action of the restoring force of the return pressure spring 45 to complete the reset. After the staple is fired, release the first handle 1, the second handle 2 will also return to the insurance position under the restoring force of the first torsion spring 31. The first handle 1 is engaged with the second handle 2 under the action of the slider, therefore, the first handle 1 will firstly reset along with the second handle 2, and at the same time, reset under the action of the second torsion spring 34.

Further, in this embodiment, a metal sheet 77 is disposed at a position inside the casing 74 of the stapler, corresponding to the first end 811 of the first indicator 81. When returns to the initial position, the first indicator 81 will strike the metal sheet 77 and emit a sound to remind the operator that the indicator has been reset.

In this embodiment, both the first handle 1 and the second handle 2 rotate around the first pin 31, therefore, rotation centers of the first handle 1 and the second handle 2 are unified, the operator's experience is better. The rotation center is unchanged in the invalid state and the firing state, at the same time, the opening of the handle can be designed smaller, the appearance is better, and the structure of the handle assembly and the stapler is more stable. Meanwhile, the pulling sheet contact portion 23 can be closer to the pulling sheet contact point, the pulling sheet 6 can be ejected more easily, and the condition of the indicator not returned caused by unsuccessful ejection will be less likely to happen.

However, the present disclosure is not limited to this, the first handle 1 and the second handle 2 may be connected in other ways, which is all within the protection scope of the present disclosure. For example, the second torsion spring and the second pin for restoring the first handle can be replaced with at least one pressure spring, the pressure spring is connected between the first handle and the casing of the stapler. The pressure spring will be deformed when the first handle is rotated, and the pressure spring will be restored, making the first handle restored, when the first handle is released. Further, double rotation centers may also be adopted, for example, a first torsion spring and a first pin shaft are provided, and a second torsion spring and a second pin shaft are also provided. The first pin is fixed to the second handle and passes through the first handle, the first torsion spring is sleeved on the first pin, and two ends of the first torsion spring are pressed against the first handle and the second handle, respectively, to realize the reset of the first handle. The second pin is fixed to the casing of the stapler and passes through the second handle, the second torsion spring is sleeved on the second pin, and two ends of the second torsion spring are pressed against the second handle and the casing of the stapler, respectively, to realize the reset of the second handle. The first handle and the second handle are rotated around the first torsion spring and the second torsion spring, respectively.

Figure 25:
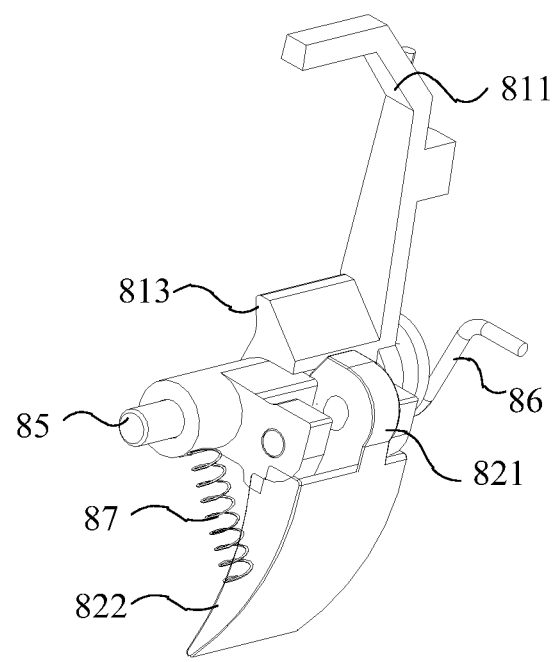
FIG. 25 is a schematic view of the indicator with a tension spring instead of a third torsion spring according to the first embodiment of the present disclosure.

Only an optional structure of the indicator is described here as an example, and the present disclosure is not limited hereto. Other variant structures are also possible. For example, as shown in FIG. 25, the third torsion spring 84 can be replaced with a tension spring 87 disposed between the first indicator 81 and the second indicator 82. When the second indicator 82 is rotated counterclockwise relative to the first indicator 81, the tension spring 87 is pulled to deform, and after the external force is released, the tension spring 87 is returned and the second indicator 82 is pulled back.

FIGS. 26 to 36 are schematic views of a handle assembly according to a second embodiment of the present disclosure. This embodiment differs from the previous embodiment in that the second indicator 82 has no indicator return member, that is, the first end of the second indicator 82 is not provided with the third pin 83 and the third torsion spring 84. In this embodiment, the reset mechanism of the second indicator 82 is that the second indicator 82 is an elastic indicator.

FIGS. 27-30 show the structure of the indicator in different states. When the first indicator 81 is rotated clockwise, the second indicator 82 can be driven to rotate clockwise, simultaneously, that is, the indicator can be rotated to the position shown in broken lines in FIG. 28. When the second end 822 of the second indicator 82 receives a rightward force, it will be rotated counterclockwise relative to the first indicator 81, therefore, the second indicator 82 is elastically deformed. The second indicator 82 can be rotated to the position shown in dotted lines in FIG. 29. However, after the rightward force is released, the second indicator 82 can return to the initial state shown in solid lines in FIG. 29, depending on its own elastic features. Therefore, the indicator will not block the movement path of the slider 42 when the first handle 1 and the second handle 2 are rotated. When the slider 42 is in the second section 412 of the sliding slot 41 and the first handle 1 is rotated counterclockwise, the slider 42 will be rotated accordingly. At this time, the indicator still has a leftward force to the slider 42 and the slider 42 will avoid the indicator. As the first handle 1 continues to rotate, the slider 42 is pressed against the handle contact portion 25, and the slider 42 is blocked by the second handle 2 and cannot continue to avoid the indicator. If an integral indicator that cannot elastically deformed is used, the indicator will block the movement path of the slider 42, which will cause the rotating and firing process of the second handle 2 not smooth, and the user experience not good.

Therefore, the present disclosure divides the indicator into two parts: the first indicator 81 and the second indicator 82, when the slider 42 cannot continue to avoid the indicator, the second end 822 of the second indicator 82 will rotate counterclockwise to avoid the slider 42 under the action of the slider 42, the rotation process will cause the second indicator 82 elastically deformed. After the first handle 1 is released, the second indicator 82 can return to the initial position by rotating clockwise under the action of the elastic features of the second indicator 82. Therefore, by adopting this structure, the problem of the handle movement being not smooth when the stapler is fired caused by the integral indicator is solved. The firing of the second handle 2 will not be affected wherever the indicator is. The indicator is allowed to interfere with other components when designing the stapler, therefore, a more compact structure of the stapler can be achieved. The second indicator 82 may be made of elastic resin, rubber material or metal material, but it is not limited to these, and other materials with a certain rigidity and elastic features can also be selected as needed.

Figure 26:
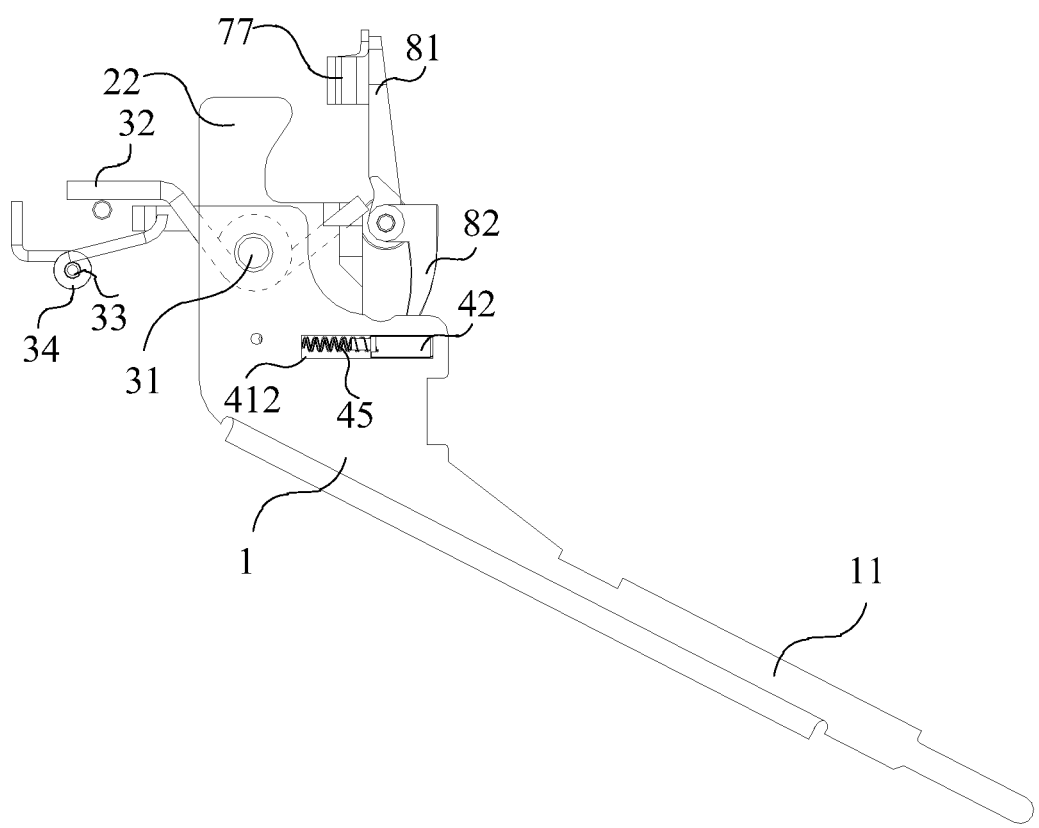
FIG. 26 is a schematic view of a handle assembly according to a second embodiment of the present disclosure.
Figure 27:
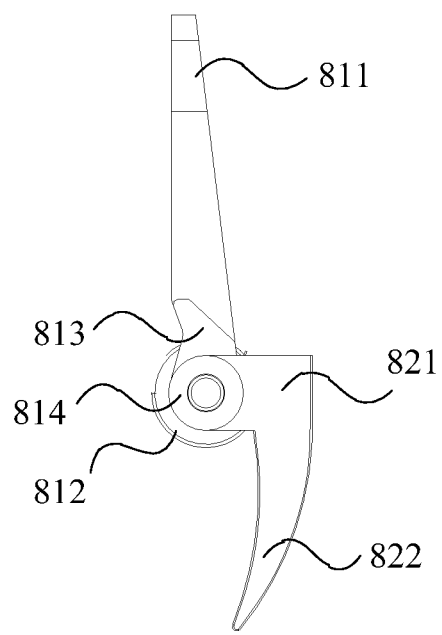
FIG. 27 is a front view of an indicator according to the second embodiment of the present disclosure.
Figure 31:
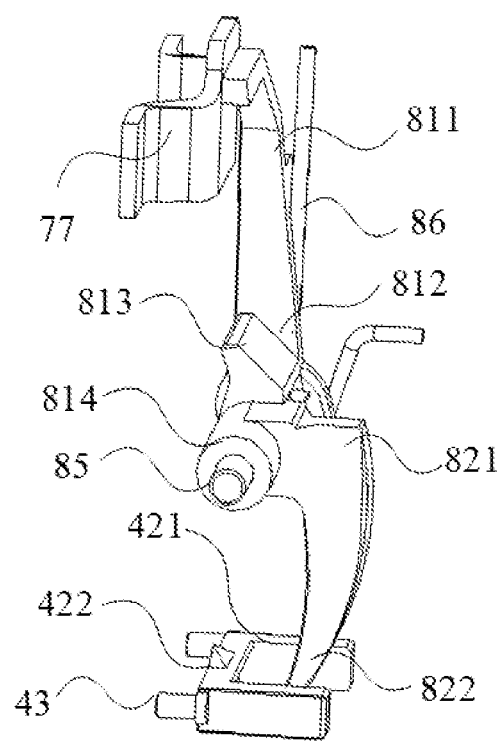
FIG. 31 is a schematic view of the indicator in the initial state according to the second embodiment of the present disclosure.
Figure 32:
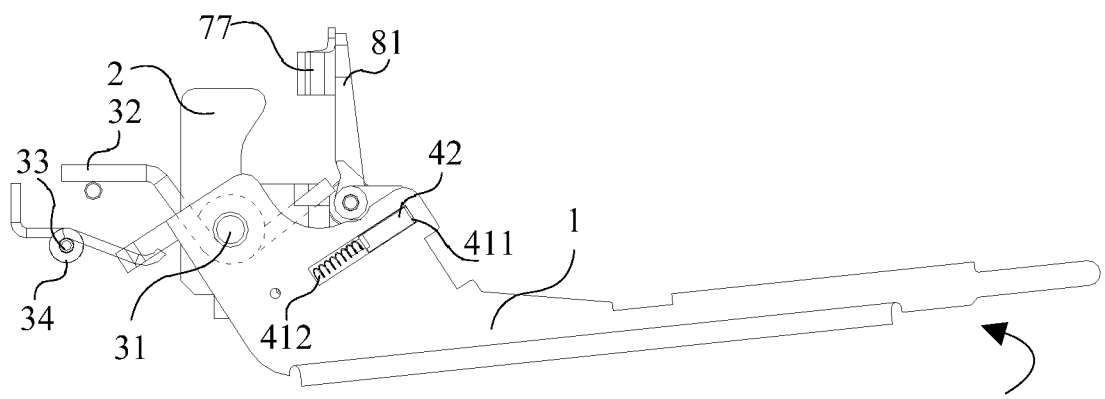
FIG. 32 is a schematic view of the handle assembly in the invalid state according to the second embodiment of the present disclosure.
Figure 33:
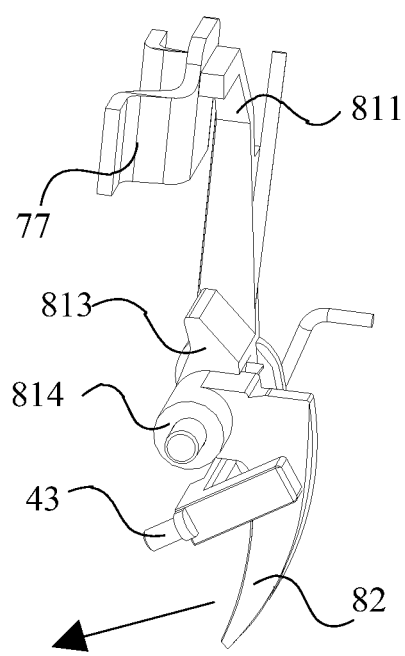
FIG. 33 is a schematic view of the handle assembly in the invalid state according to the second embodiment of the present disclosure.

FIGS. 26 and 31 show the structure of the handle assembly in the initial state according to the second embodiment. FIGS. 32 and 33 show the structure of the handle assembly in the invalid state of this embodiment. In the invalid state, the first indicator 81 is not pushed by the pulling sheet 6, so the position of the first indicator 81 is not changed, the first end 811 of the first indicator 81 is in the first position area, and the second indicator 82 has no force on the slider 42. The slider 42 is still in the first section 411 of the sliding slot 41, and the slider 42 does not interfere with the handle contact portion 25 of the second handle 2 on the rotation path of the first handle 1. At this time, the device is in the insurance state. When the operator presses the first handle 1, the first handle 1 can be easily rotated, but the second handle 2 will not be driven to rotate, thereby the firing of the stapler cannot be completed. The operator can also get a tactile feedback at this time, knowing that the first indicator 81 currently has not reached the position indicating the stapler being ready to be fired, and the stapler is not fired.

Figure 28:
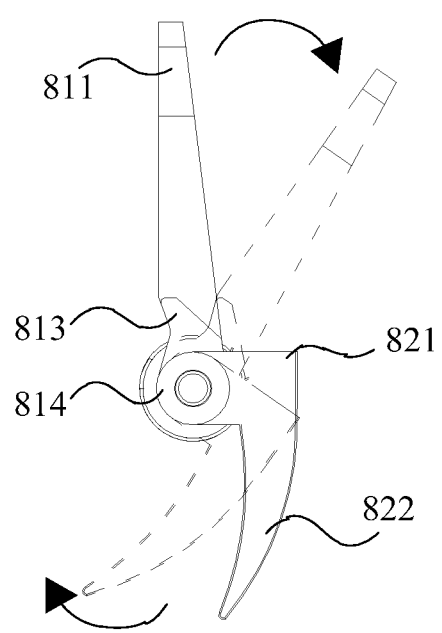
FIG. 28 is a schematic view of the indicator rotating in the first direction according to the second embodiment of the present disclosure.
Figure 29:
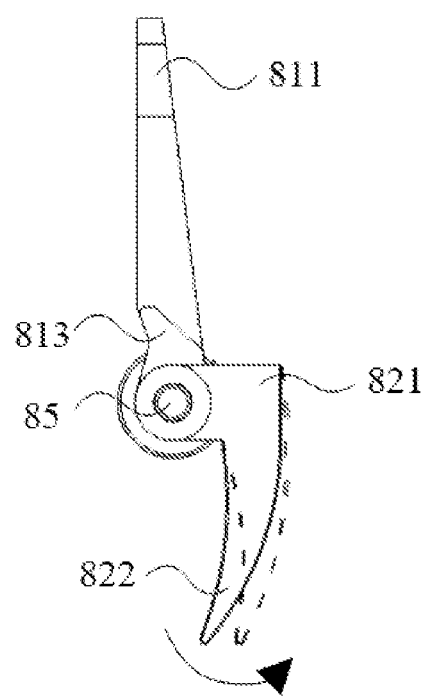
FIG. 29 is a schematic view of a second indicator rotating in the second direction according to the second embodiment of the present disclosure.
Figure 30:
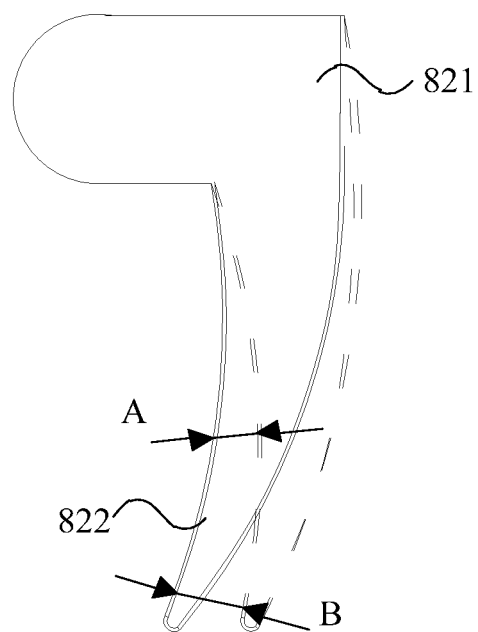
FIG. 30 is a schematic view of the second indicator according to the second embodiment of the present disclosure.

At this time, although the slider 42 is pressed against the second indicator 82, the slider 42 can be pushed by the second indicator 82 to move a small displacement in the direction along the arrow in FIG. 28, to avoid the indicator, since the force of the return pressure spring 45 is smaller than the force of the second indicator 82 against the elastic deformation.

Figure 34:
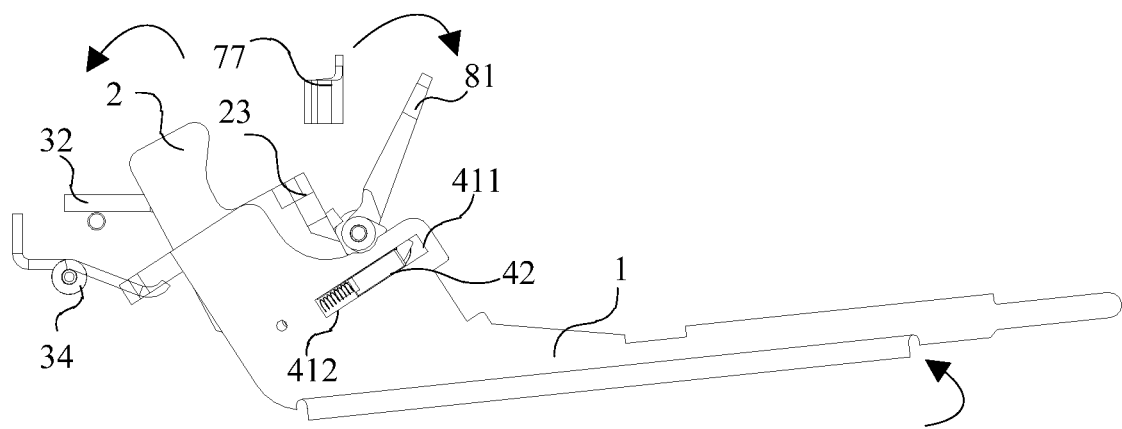
FIG. 34 is a schematic view of the handle assembly in the firing state according to the second embodiment of the present disclosure.
Figure 35:
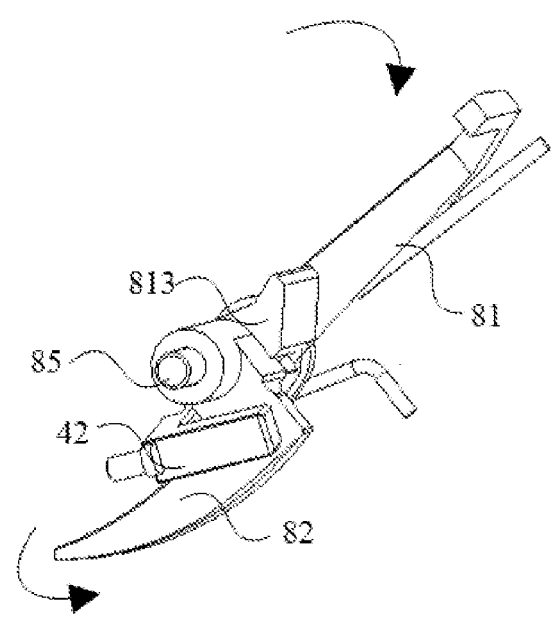
FIG. 35 is a schematic view of the handle assembly in the firing state according to the second embodiment of the present disclosure.
Figure 36:
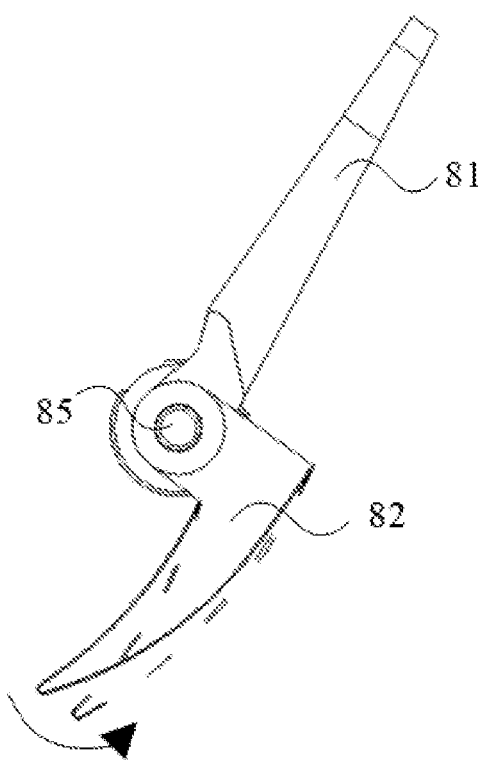
FIG. 36 is a schematic view of the handle assembly in the firing state according to the second embodiment of the present disclosure.

FIGS. 34 to 36 show the structure of the handle assembly in the firing state according to the second embodiment. In this process, rotating the knob 71, the pulling sheet 6 is driven by the screw rod 76 to move toward the proximal end of the stapler. The first indicator 81 is driven to move in the clockwise direction to the second position area, therefore, and the slider 42 is pushed by the second indicator 82 to move to the second section 412 of the sliding slot 41 until interfere with the handle contact portion 25. When the first handle 1 is pressed to rotate counterclockwise, the slider 42 is pressed against the handle contact portion 25 and blocks the second handle 2 from continuing to enter the internal cavity of the first handle 1. As a result, the second handle 2 and the first handle 1 become linked. The second handle 2 is rotated counterclockwise along with the first handle 1, the staple pushing rod 75 is pushed by the second end 22 of the second handle 2, and the staple pushing rod 75 will further push the stapler pushing sheet and the circular cutter of the stapler, to suture and cut the tissues to be operated.

The return pressure spring 45 for the slider is gradually compressed during the movement process of the slider 42. The movement process of the slider 42 is divided into two steps: firstly, when the slider 42 is not pressed against the second handle 2, the slider 42 will avoid the second indicator 82 since the force of the second indicator 82 against elastic deformation is much greater than the force exerted by the return pressure spring 45 on the slider 42; secondly, after the slider 42 is pressed against the second handle 2, the slider 42 cannot continue to avoid the indicator due to the force between the second handle 2 and the first handle 1. Therefore, the second end 822 of the second indicator 82 will be pushed to rotate counterclockwise, to realize that the second indicator 82 avoids the slider 42. The deformation process of the second indicator 82 can be seen in FIGS. 35 and 36. After the stapler is fired, the first handle 1 is released, the slider 42 will be pushed to move toward the first section 411 of the sliding slot 41 again and return to the initial position, under the deformation force of the return pressure spring 45 returning to its initial state. The second indicator 82 is no longer pushed by the slider 42 and can restore to the initial state depending on its own elastic deformation restoring effect.

The structure of the elastic second indicator 82 in the second embodiment can also be combined with various features in the first embodiment to form new technical solutions, which are all within the protection scope of the present disclosure. The firing and restoring processes of the first handle 1 and the second handle 2 are similar to the first embodiment, and will not be repeated here.

The embodiment of the present disclosure also provides a stapler including the handle assembly. When the stapler is not ready to be fired, the second handle cannot be actuated by the first handle and the stapler cannot be fired. The doctor can also judge the firing state through his operating experience. Only when the stapler is ready to be fired, the movement of the first handle will actuate the movement of the second handle and then fire the stapler. Therefore, the stapler is prevented from being fired by mistake, and the cracking of the stapler is avoided from being cracked at the same time. The indicator is divided into the first indicator and the second indicator rotatably connected, which solves the problem caused by the integral indicator that the handle movement being not smooth when the stapler is fired is solved. The firing of the second handle will not be affected wherever the indicator is. The indicator is allowed to interfere with other components when designing the stapler, to achieve a more compact structure of the stapler and a smoother firing process.

The handle assembly and the stapler including the same provided by the present disclosure have the following advantages.

The present disclosure provides a handle assembly and a stapler including the same, the handle assembly includes the first handle and the second handle, and only the movement of the second handle can fire the stapler to perform cutting and suturing actions. During operation, the first handle can be pressed by the doctor whether the stapler is ready to be fired or not. When the stapler is not ready to be fired, the second handle cannot be actuated by the first handle and the stapler cannot be fired. The indicator includes the first indicator and the second indicator, the second indicator can be pushed to rotate by the slider when the first handle and the second handle are rotated together. Therefore, the indicator will not block the rotation of the handle assembly, which ensures smooth movement of the stapler when the stapler is fired and improves user experience. Meanwhile, the second indicator can return to the initial position through the indicator return member when the firing is completed.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A handle assembly for firing a stapler, comprising:
a first handle and a second handle, wherein, a sliding slot is disposed on the first handle, the sliding slot comprises a first section and a second section connected with each other, a slider is slidably disposed in the sliding slot, the first handle and the second handle are not linked when the slider is in the first section of the sliding slot;
a first indicator and a second indicator, wherein, the first indicator is connected to a first end of the second indicator; a second end of the second indicator is driven to rotate in a first direction and the slider is pushed to move from the first section of the sliding slot to the second section of the sliding slot, when the first indicator is rotated in the first direction;
wherein, the second handle is linked with the first handle and the second end of the second indicator is pushed by the slider to rotate in a second direction, when the slider is in the second section of the sliding slot and pressed against the second handle due to rotation of the first handle in the second direction.

2. The handle assembly of claim 1, wherein the first indicator and the first end of the second indicator are rotatably connected through an indicator return member, and the indicator return member is deformed when the second end of the second indicator is pushed to rotate in the second direction by the slider.

3. The handle assembly of claim 2, wherein the indicator return member comprises a third pin and a third torsion spring sleeved on the third pin, the third pin passes through the first end of the second indicator and is fixed to the first indicator, and two ends of the third torsion spring are pressed against the first indicator and the second indicator, respectively.

4. The handle assembly of claim 3, wherein a first clamping slot for the third torsion spring is disposed on the first indicator, and a second clamping slot for the third torsion spring is disposed on the first end of the second indicator, and the two ends of the third torsion spring are embedded in the first clamping slot and the second clamping slot, respectively.

5. The handle assembly of claim 2, wherein the indicator return member comprises a third pin and a tension spring, the third pin passes through the first end of the second indicator and is fixed to the first indicator, and the tension spring is disposed between the first indicator and the second indicator.

6. The handle assembly of claim 1, wherein the second indicator is an elastic indicator, and the second indicator is deformed elastically when the second end of the second indicator is pushed to rotate in the second direction by the slider.

7. The handle assembly of claim 6, wherein the first indicator and the second indicator are integrally formed.

8. The handle assembly of claim 6, wherein the second indicator is made of elastic resin, rubber material or metal material.

9. The handle assembly of claim 1, wherein the second end of the second indicator is curved toward a distal end of the stapler relative to the first end of the second indicator, and a smooth transition is configured between the first end and the second end of the second indicator.

10. The handle assembly of claim 1, wherein a positioning portion is disposed between two ends of the first indicator, and the first indicator is rotatably connected to a casing of the stapler through the positioning portion.

11. The handle assembly of claim 10, wherein the handle assembly further comprises a fourth pin passing through the positioning part and a fourth torsion spring sleeved on the fourth pin, the fourth pin is fixed on the casing of the stapler, and two ends of the fourth torsion spring are pressed against the casing of the stapler and the first indicator, respectively.

12. The handle assembly of claim 10, wherein a projecting portion is disposed between the first end of the first indicator and the positioning portion, a second end of the first indicator is connected to the first end of the second indicator, the projecting portion is located correspondingly to a position of a pulling hook of a pulling sheet, a proximal end of the pulling sheet is sleeved on a screw rod, and a distal end of the screw rod is provided with a knob, when rotating the knob, the pulling sheet is driven to move toward a proximal end of the stapler, and the first indicator is pulled, by the pulling sheet and through the projecting portion, to rotate in the first direction;

the first handle or the second handle comprises a pulling sheet contact portion;

the pulling sheet contact portion is pressed against the pulling sheet, making the pulling hook of the pulling sheet separated from the indicator, when the first handle and the second handle are rotated in the second direction.

13. The handle assembly of claim 1, wherein the handle assembly further comprises a slider return spring disposed on the first handle; the slider return spring is in a deformation state by a force exerted by the slider, when the slider is in the second section of the sliding slot; and the slider is driven to move from the second section to the first section of the sliding slot, when the slider return spring restores from the deformation state to an initial state.

14. The handle assembly of claim 13, wherein the first indicator and the first end of the second indicator are rotatably connected through an indicator return member; a force exerted on the slider by the slider return spring is less than a force exerted on the indicator by the indicator return member, when the slider is in the second section of the sliding slot, and the second handle has not been pressed against the slider while the first handle rotating in the second direction.

15. The handle assembly of claim 13, wherein the second indicator is an elastic indicator; a force exerted on the slider by the slider return spring is less than a force formed by the second indicator resisting elastic deformation, when the slider is in the second section of the sliding slot, and the second handle has not been pressed against the slider while the first handle rotating in the second direction.

16. The handle assembly of claim 1, wherein the handle assembly further comprises:

a first torsion spring and a first pin, wherein, the first pin passes through the first handle and the second handle, and is fixed to a casing of the stapler, the first torsion spring is sleeved on the first pin, and two ends of the first torsion spring are pressed against the casing of the stapler and the second handle, respectively;

a second torsion spring and a second pin, wherein, the second pin is fixed to the casing of the stapler, the second torsion spring is sleeved on the second pin, and two ends of the second torsion spring are pressed against the casing of the stapler and the first handle, respectively.

17. The handle assembly of claim 1, wherein the handle assembly further comprises:

a first torsion spring and a first pin, wherein, the first pin passes through the first handle and the second handle, and is fixed to a casing of the stapler, the first torsion spring is sleeved on the first pin, and two ends of the first torsion spring are pressed against the casing of the stapler and the second handle, respectively;

a handle return pressure spring connected between the first handle and the casing of the stapler.

18. The handle assembly of claim 1, wherein the handle assembly further comprises:

a first torsion spring and a first pin, wherein, the first pin is fixed to the second handle and passes through the first handle, the first torsion spring is sleeved on the first pin, and two ends of the first torsion spring are pressed against the first handle and the second handle, respectively;

a second torsion spring and a second pin, wherein, the second pin is fixed to a casing of the stapler and passes through the second handle, the second torsion spring is sleeved on the second pin, and two ends of the second torsion spring are pressed against the second handle and the casing of the stapler, respectively.

19. A stapler, comprising the handle assembly of claim 1.

\* \* \* \* \*